US007741068B2

(12) United States Patent
Hess et al.

(10) Patent No.: US 7,741,068 B2
(45) Date of Patent: *Jun. 22, 2010

(54) METHODS FOR DIFFERENTIATION BETWEEN CARDIAC AND PULMONARY CAUSES OF CHRONIC DYSPNEA

(75) Inventors: Georg Hess, Mainz (DE); Andrea Horsch, Mannheim (DE)

(73) Assignee: Roche Diagnostics Operations, Inc., Indianapolia, IN (US)

( * ) Notice: Subject to any disclaimer, the term of this patent is extended or adjusted under 35 U.S.C. 154(b) by 375 days.

This patent is subject to a terminal disclaimer.

(21) Appl. No.: 11/784,769

(22) Filed: Apr. 9, 2007

(65) Prior Publication Data

US 2009/0111138 A1    Apr. 30, 2009

(30) Foreign Application Priority Data

Apr. 13, 2006  (EP) .................................. 06112620

(51) Int. Cl.
C12Q 1/37    (2006.01)
(52) U.S. Cl. ........................................................ 435/24
(58) Field of Classification Search .................... 435/24
See application file for complete search history.

(56) References Cited

U.S. PATENT DOCUMENTS

| 5,744,305 | A | 4/1998 | Fodor et al. | |
|---|---|---|---|---|
| 2006/0166276 | A1* | 7/2006 | Doyle et al. | 435/7.1 |
| 2007/0269836 | A1* | 11/2007 | McPherson et al. | 435/7.4 |
| 2008/0070315 | A1* | 3/2008 | Hess et al. | 436/86 |

FOREIGN PATENT DOCUMENTS

| EP | 0 648 228 B1 | | 11/1998 |
|---|---|---|---|
| WO | WO 02/083913 A1 | | 10/2002 |
| WO | WO 02/089657 A2 | | 11/2002 |
| WO | WO 2004/059293 | * | 7/2004 |
| WO | WO 2004/059293 A2 | | 7/2004 |
| WO | WO 2004/077056 | * | 9/2004 |
| WO | WO 2004/077056 A1 | | 9/2004 |

OTHER PUBLICATIONS

Doyle, I.R., et al.; Surfactant Proteins-A and -B Are Elevated in Plasma of Patients with Acute Respiratory Failure; Am J Respir Crit Care Med, vol. 156, 1997, pp. 1217-1229.
Nielsen, Svendstrup L., et al.; N-terminal pro-brain natriuretic peptide for discriminating between cardiac and non-cardiac dyspnoea; The European Journal of Heart Failure 6, Elsevier, 2004, pp. 63-70.
Dowdy and Wearden; Statistics for Research; John Wiley & Sons, New York, Chapter II, 1983, pp. 173-200.
Nolan, J.P., et al.; Suspension array technology: evolution of the flat-array paradigm; Trends in Biotechnology, vol. 20, No. 1, Jan. 2002, pp. 9-12.

Hawgood, S.; Pulmonary surfactant apoproteins: a review of protein and genomic structure; Am. J. Physiol.—Lung Cellular and Molecular Physiology, vol. 257, Issue 2, 1989, pp. L13-L22.
Takahashi, H., et al.; Pulmonary Surfactant Proteins A and D: Innate Immune Functions and Biomarkers for Lung Diseases; Current Pharmaceutical Design, vol. 12, No. 5., 2006, pp. 589-598.
Kurutz, J.W., et al.; NMR Structure of Lung Surfactant Peptide SP-B11-25; Biochemistry, vol. 41, No. 30, 2002, pp. 9627-9636.
Guttentag, S., et al.; Surfactant protein B processing in human fetal lung; Am. J. Physiol.—Lung Cellular and Molecular Physiology, vol. 275, Issue 3, 1998, pp. L559-L566.
Bonow, R.O.; New Insights Into the Cardiac Natriuretic Peptides; Circulation, vol. 93, No. 11, Jun. 1, 1996, pp. 1946-1950.
Smith, M. W., et al.; Delayed metabolism of human brain natriuretic peptide reflects resistance to neutral endopeptidase; Journal of Endocrinology, 167, 2000, pp. 239-246.
Mueller, T., et al.; Long-term stability of endogenous B-type natriuretic peptid (BNP) and amino terminal proBNP (NT-proBNP) in frozen plasma samples; Clin Chem Lab Med, 42, 2004, pp. 942-944.
Wu, A. H.B., et al.; Analytical and Clinical Evaluation of the Bayer ADVIA Centaur Automated B-Type Natriuretic Peptide Assay in Patients with Heart Failure: A Multisite Study; Clin Chem 50:5, 2004, pp. 867-873.
Karl, J., et al; Development of a novel, N-Terminal-proBNP (NT-proBNP) assay with a low detection limit; Scand J Clin Lab Invest, 59 (Suppl. 230), 1999, pp. 177-181.
Yeo, Kiang-Teck J., et al.; Multicenter evaluation of the Roche NT-proBNP assay and comparison to the Biosite Triage BNP assay; Clinica Chimica Acta 338, Elsevier, 2003, pp. 107-115.
El Mahmoud, R., et al.; Type B natriuretic peptide (BNP) versus n-terminal type B natriuretic propeptide in the diagnosis of cardiac failure in the elderly over 75 population; Arch Mal Coeur Vaiss 99(3), Mar. 2006, p. 201-7.
De Pasquale, C.G., et al.; Plasma Surfactant Protein-B: A Novel Biomarker in Chronic Heart Failure (HF); ACC Current Journal Review, vol. 14, No. 2, Feb. 2005, p. 33.

\* cited by examiner

*Primary Examiner*—Ralph Gitomer
(74) *Attorney, Agent, or Firm*—Marilyn Amick; Roche Diagnostics Operations, Inc.

(57) ABSTRACT

The present invention relates to a method for differentiating in a subject suffering from chronic shortness of breath (dyspnea) between (i) a pulmonary disease, (ii) a cardiovascular complication, (iii) a cardiovascular complication accompanied by a pulmonary disease and (iv) dyspnea without cardiovascular or pulmonary causes. The method comprises the steps of determining an amount of a pulmonary surfactant protein in a sample of a subject, determining an amount of a natriuretic peptide in a sample of said subject, and differentiating between (i) a pulmonary disease, (ii) a cardiovascular complication, (iii) a cardiovascular complication accompanied by a pulmonary disease and (iv) chronic dyspnea without cardiovascular or pulmonary causes by comparing the amount determined in a) and the amount determined in b) with a reference amount for each. The present invention further provides a device and a kit for carrying out the inventive methods.

11 Claims, 2 Drawing Sheets

SEQUENCE LISTING

```
<160> NUMBER OF SEQ ID NOS: 1

<210> SEQ ID NO 1
<211> LENGTH: 76
<212> TYPE: PRT
<213> ORGANISM: homo sapiens

<400> SEQUENCE: 1

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
        35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75
```

METHODS FOR DIFFERENTIATION BETWEEN CARDIAC AND PULMONARY CAUSES OF CHRONIC DYSPNEA

CROSS REFERENCE TO RELATED APPLICATIONS

This application claims priority to EP 06112620.7 filed Apr. 13, 2006 and which is herein incorporated fully by reference.

TECHNICAL FIELD

The present invention relates to diagnostic methods and means. Specifically, it relates to a method for differentiating cause in a subject suffering from chronic shortness of breath (dyspnea) between (i) a pulmonary disease, (ii) a cardiovascular complication, (iii) a cardiovascular complication accompanied by a pulmonary disease and (iv) dyspnea without cardiovascular or pulmonary causes. The method comprises the steps of determining an amount of a pulmonary surfactant protein in a sample from a subject, determining an amount of a natriuretic peptide in a sample from the subject, and differentiating between (i) a pulmonary disease, (ii) a cardiovascular complication, (iii) a cardiovascular complication accompanied by a pulmonary disease or (iv) chronic dyspnea without cardiovascular or pulmonary causes, by comparing the amount determined in a) and the amount determined in b) with a reference amount. The present invention further relates to devices and kits for carrying out the inventive methods.

BACKGROUND OF THE INVENTION

Cardiovascular complications and, in particular, acute cardiovascular events are most often life threatening medical conditions which require immediate action. However, these conditions can not always be unambiguously diagnosed. Specifically, some of the most common symptoms accompanying various types of heart diseases including acute cardiovascular events, but also chronic heart dysfunctions such as chronic heart failure, are symptoms which are characteristic for other (non-cardiovascular) diseases as well. Therefore, it is often difficult, cumbersome and time consuming to differentiate between a cardiovascular or other cause of an observed symptom. Differentiation may also require the help of a specialist such as a cardiologist.

A typical symptom for cardiovascular complications, and, in particular, for an acute cardiovascular event or a more severe chronic heart failure, is shortness of breath (dyspnea). As for other symptoms, dyspnea may have various causes including cardiovascular complications and non-cardiovascular pulmonary diseases. In light of a potential cardiovascular cause of the symptom, though, it is very important to properly diagnose its cause in a given patient, e.g., an emergency patient.

As disclosed in WO2004/077056, systemic levels of surfactant proteins may be used as markers for heart failure. However, the disclosed techniques do not allow for a differential diagnosis of the cause of the elevated levels of the surfactant proteins. Specifically, it is known that pulmonary diseases or damages may also result in increased systemic levels of the proteins (Doyle 1997, Am J Respir Crit Care Med Vol. 156: 1217-1229). Accordingly, the '056 disclosed methods are highly likely to produce false positive diagnostic results, which, in turn, result in an application of inappropriate therapeutic regimen (Svendstrup Nielsen, 2004, The European Journal of Heart Failure 6: 63-70).

Therefore, there is a clear and long-standing need for means and methods permitting a differential diagnosis of the cause of symptoms such as dyspnea and, in particular, chronic dyspnea, in a subject. Desirable means and methods allow a reliable and efficient diagnosis while avoiding the drawbacks of the current techniques.

The technical problem underlying the present invention is the provision of means and methods for complying with the aforementioned needs. The technical problem is solved by the present invention as defined by the claims and as set forth below.

BRIEF DESCRIPTION OF THE FIGURES

The figures are provided to illustrate certain embodiments of the present invention and should not be construed as limiting the scope of invention as defined by the claims.

DETAILED DESCRIPTION OF THE INVENTION

Figure 1:
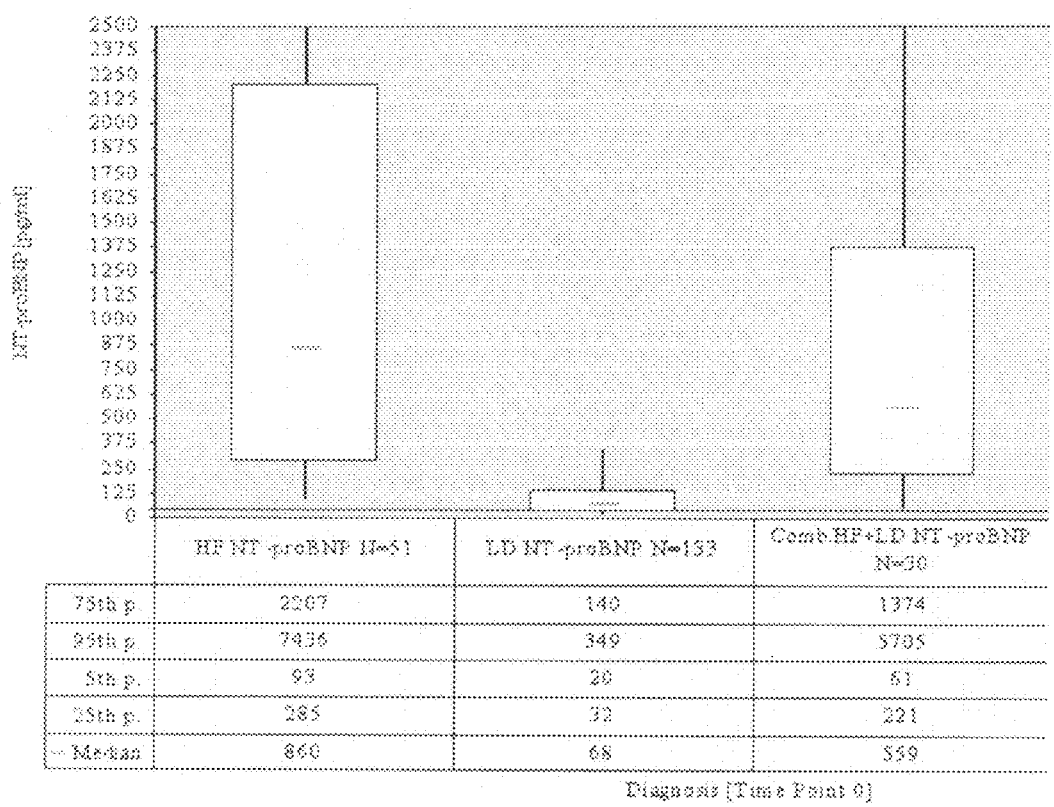
FIG. 1: The figure shows box plots for the NT-proBNP concentration measured for a patient cohort having either heart failure (HF), a pulmonary disease (LD) or both (Comb. HF+LD). N represents the number of patients. Moreover, indicated are the median and the 75th, 95th, 5th and 25th percentiles.

Accordingly, one embodiment of the present invention relates to a method for differentiating cause in a subject suffering from chronic shortness of breath (dyspnea) between (i) a pulmonary disease, (ii) a cardiovascular complication, (iii) a cardiovascular complication accompanied by a pulmonary disease and (iv) dyspnea without cardiovascular or pulmonary causes. The method comprises the steps of:

determining an amount of a pulmonary surfactant protein (SP) in a sample of a subject;

determining an amount of a natriuretic peptide in a sample of said subject; and differentiating between (i) a pulmonary disease, (ii) a cardiovascular complication, (iii) a cardiovascular complication accompanied by a pulmonary disease or (iv) dyspnea without cardiovascular or pulmonary causes by comparing the amounts determined in a) and b) with reference amounts.

In a preferred embodiment, the method of the present invention is an in vitro method. Moreover, it is understood that the inventive methods may comprise steps in addition to those explicitly referred to above such as further sample pretreatment steps or evaluation steps.

The term "differentiating" as used herein means to distinguish between a subject which suffers from (i) a pulmonary disease, (ii) a cardiovascular complication, (iii) a cardiovascular complication accompanied by a pulmonary disease or (iv) dyspnea without cardiovascular or pulmonary causes under conditions where the subjects suffering from said disease show essentially the same symptoms, i.e. chronic shortness of breath. The term as used herein, preferably, includes differentially diagnosing a pulmonary disease, a cardiovascular complication showing pulmonary symptoms, a cardiovascular complication accompanied by a pulmonary disease or chronic dyspnea without cardiovascular or pulmonary causes. As used herein, to "cause" a symptom means to contribute directly or indirectly to the presence or severity of a symptom in a subject exhibiting the symptom.

Diagnosing as used herein refers to assessing the probability of a subject suffering from the diseases referred to in this specification. As will be understood by those skilled in the art, such an assessment is usually not contemplated to be correct for 100% of the subjects to be diagnosed. The term, however, requires that a statistically significant portion of subjects can be diagnosed to suffer from the disease (e.g. a cohort in a cohort study). Whether a portion is statistically significant can be determined using methods well known by a person of ordinary skill in the art, including various well known statistic evaluation tools, e.g., determination of confidence intervals, p-value determination, Student's t-test, Mann-Whitney test etc.. Details are found in Dowdy and Wearden, Statistics for Research, John Wiley & Sons, New York 1983. Preferred confidence intervals are at least 90%, at least 95%, at least 97%, at least 98% or at least 99%. The p-values according to the present invention are, preferably, 0.1, 0.05, 0.01, 0.005, or 0.0001.

Diagnosing according to the present invention also includes monitoring, confirming, sub-classifying and predicting the relevant disease, symptoms or risks therefor. Monitoring relates to keeping track of an already diagnosed disease, or complication, e.g. to analyze the progression of the disease or the influence of a particular treatment on the progression of disease or complication. Confirmation or confirming relates to the strengthening or substantiating a diagnosis already performed using other indicators or markers. Sub-classification or sub-classifying relates to further defining a diagnosis according to different subclasses of the diagnosed disease, e.g. defining according to mild and severe forms of the disease. Prediction or predicting relates to prognosing a disease or complication before other symptoms or markers have become evident or have become significantly altered.

The expression "chronic shortness of breath" or "chronic dyspnea" refers to an impaired respiration which results in an increased respiratory frequency and/or an increased respiratory volume. Thus, according to one specific embodiment, shortness of breath may result in hyperventilation. Typically, shortness of breath occurs at an oxygen saturation level below the normal oxygen saturation level of at least 95%. Chronic dyspnea as used herein refers to permanent or permanently occurring shortness of breath (i.e. shortness of breath which repeatedly occurs under the same conditions).

The term "pulmonary disease" refers to a disease which causes shortness of breath. Moreover, it is envisaged that a pulmonary disease as referred to in accordance with the present invention results in an impaired alveolocapillary membrane barrier having an increased permeability for surfactant proteins, in particular for the pulmonary surfactant protein specifically referred to herein. According to specific embodiments, the disease is acute and chronic respiratory failure, pulmonary fibrosis, pulmonary proteinosis, pulmonary oedema, pulmonary inflammation, pulmonary emphysema obesity, thyroid diseases or, more preferably, a pulmonary embolism.

The term "cardiovascular complication" as used herein refers to any acute or chronic disorder of the cardiovascular system. Acute disorders of the cardiovascular system include acute cardiovascular events. Thus, more specific embodiments include stable angina pectoris (SAP) or acute coronary syndromes (ACS). ACS patients can show unstable angina pectoris (UAP) or, in the event these individuals have already suffered from a myocardial infarction (MI), the MI can be an ST-elevated MI or a non-ST-elevated MI. The occurring of an MI may be followed by a left ventricular dysfunction (LVD). Also encompassed by the term are chronic disorders and, more specifically, heart failure. It is to be understood that the term also includes medical conditions and diseases which cause heart failure in addition to the aforementioned acute cardiovascular events, such as congenital or acquired heart valve diseases or disorders, myocarditis, myocardiopathy, amyloidosis or hemochromatosis. Further specific cardiovascular diseases are thrombosis, for example, arterial thrombosis, or diseases causing blood vessel calcification, for example, atherosclerosis, as well as stroke.

Individuals suffering from a cardiovascular complication may show clinical symptoms (e.g. dyspnea, chest pain, see also NYHA classification below). Specifically, symptoms of cardiovascular diseases have been classified into a functional classification system according to the New York Heart Association (NYHA). Patients of Class I have no obvious symptoms of cardiovascular disease. Physical activity is not limited, and ordinary physical activity does not cause undue fatigue, palpitation, or dyspnea. Patients of class II have slight limitation of physical activity. They are comfortable at rest, but ordinary physical activity results in fatigue, palpitation, or dyspnea. Patients of class III show a marked limitation of physical activity. They are comfortable at rest, but less than ordinary activity causes fatigue, palpitation, or dyspnea. Patients of class IV are unable to carry out any physical activity without discomfort. They show symptoms of cardiac insufficiency at rest. If any physical activity is undertaken, discomfort is increased. Another characteristic of cardiovascular complication can be the "left ventricular ejection fraction" (LVEF) which is also known as "ejection fraction". People with a healthy heart usually have an unimpaired LVEF, which is generally described as above 50%. Most people with a systolic heart disease which is symptomatic generally have an LVEF of 40% or less.

According to specific embodiments of the present invention, a subject suffering from a cardiovascular complication and exhibiting chronic dyspnea in accordance with the present invention can be allocated to an NYHA class, specifically, to NYHA class I, II or III and, more specifically, to NYHA class II.

By "a cardiovascular complication accompanied by a pulmonary disease" it is meant that the subject suffers from a cardiovascular complication and from a pulmonary disease. It is to be understood that the two diseases or disorders may appear independently, i.e. without one causing the other. However, cases in which a primary cardiovascular complication as referred to herein causes a secondary pulmonary diseases and vice versa are also, preferably, encompassed from the above expression.

Further, chronic dyspnea may be observed in patients which neither suffer from cardiovascular complications nor from pulmonary diseases. Such cases shall be comprised by the term "chronic dyspnea without cardiovascular or pulmonary causes" for the purpose of the present invention. Specifically contemplated non-cardiovascular and non-pulmonar causes of shortness of breath are, preferably, obesity, high body weight, an untrained or poorly trained physical condition of the subject, psychological conditions such as anxiety states.

The term "subject" as used herein relates to animals, preferably mammals, and, more preferably, humans. According to a specific embodiment, it is envisaged by the present invention that the subject exhibits chronic shortness of breath.

Determining the amount of a natriuretic peptide or a pulmonary surfactant protein according to the present invention relates to measuring the amount or concentration, preferably semi-quantitatively or quantitatively. Measuring can be done directly or indirectly. Direct measuring relates to measuring the amount or concentration of the natriuretic peptide or the pulmonary surfactant protein based on a signal which is obtained from the natriuretic peptide or the pulmonary surfactant protein itself and the intensity of which directly correlates with the number of molecules of the peptide present in the sample. Such a signal—sometimes referred to herein as intensity signal—may be obtained, e.g., by measuring an intensity value of a specific physical or chemical property of the natriuretic peptide or the pulmonary surfactant protein. Indirect measuring includes measuring of a signal obtained from a secondary component (i.e. a component not being the natriuretic peptide itself) or a biological read out system, e.g., measurable cellular responses, ligands, labels, or enzymatic reaction products.

In accordance with the present invention, determining the amount of the natriuretic peptide or the pulmonary surfactant protein can be achieved by all known means for determining the amount of a peptide in a sample. Such means comprise, for example, immunoassay devices and methods which may utilize labelled molecules in various sandwich, competition, or other assay formats. The assays will develop a signal which is indicative for the presence or absence of the natriuretic peptide or the pulmonary surfactant protein. Moreover, the signal strength can, preferably, be correlated directly or indirectly (e.g. reverse-proportional) to the amount of polypeptide present in a sample. Further suitable methods comprise measuring a physical or chemical property specific for the natriuretic peptide such as its precise molecular mass or NMR spectrum. Exemplary methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

In a preferred embodiment, the method for determining an amount of a natriuretic peptide or a pulmonary surfactant protein comprises the steps of (a) contacting a cell capable of eliciting a cellular response the intensity of which is indicative of the amount of the peptide with the peptide for an adequate period of time, (b) measuring the cellular response.

For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide.

In another preferred embodiment, the method for determining the amount of a natriuretic peptide or a pulmonary surfactant protein comprises the step of measuring a specific intensity signal obtainable from the natriuretic peptide or a pulmonary surfactant protein in the sample.

As described above, such a signal may be the signal intensity observed at an m/z variable specific for the natriuretic peptide or a pulmonary surfactant protein observed in mass spectra or a NMR spectrum specific for the natriuretic peptide or a pulmonary surfactant protein.

In another preferred embodiment, the method for determining the amount of a natriuretic peptide comprises the steps of (a) contacting the peptide with a specific ligand, (b) (optionally) removing non-bound ligand, (c) measuring the amount of bound ligand.

The bound ligand will generate an intensity signal. Binding according to the present invention may include both covalent and non-covalent binding. A ligand according to the present invention can be any compound, e.g., a peptide, polypeptide, nucleic acid, or small molecule, binding to the natriuretic peptide or the pulmonary surfactant protein described herein. Preferred ligands include antibodies, nucleic acids, peptides or polypeptides such as receptors for the natriuretic peptides or binding partners for the pulmonary surfactant protein and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display.

Antibodies as referred to herein include both polyclonal and monoclonal antibodies, as well as fragments thereof, such as Fv, Fab and F(ab)$_2$ fragments that are capable of binding antigen or hapten. The present invention also includes humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the natriuretic peptide. Specific binding according to the present invention means that the ligand or agent should not bind substantially to ("cross-react" with) another peptide, polypeptide or substance present in the sample to be analyzed. Preferably, the specifically bound natriuretic peptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, the method is semi-quantitative or quantitative. Suitable methods include directly measuring binding of a ligand, e.g. by NMR, mass spectrometry or surface plasmon resonance. In addition, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the ligand/natriuretic peptide or ligand/pulmonary surfactant protein complex or the ligand which was bound by the natriuretic peptide or the pulmonary surfactant protein, respectively, may be contacted with a suitable substrate allowing detection by the generation of an intensity signal. For measurement of enzymatic reaction products, preferably the amount of substrate is saturating. The substrate may also be labelled with a detectable label prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g. detectable) amount of product can be measured.

In another embodiment, the ligand may be coupled covalently or non-covalently to a label allowing detection and measurement of the ligand. Labelling may be done by direct or indirect methods. Direct labelling involves coupling of the label directly (covalently or non-covalently) to the ligand. Indirect labelling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}$S, $^{125}$I, $^{32}$P, $^{33}$P and the like. A radioactive label can be detected by any method known and appropriate, e.g. a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labeling or other dectection methods as described above.

According to another specific embodiment, the method for determining the amount of a natriuretic peptide comprises (a) contacting a solid support comprising a ligand for the natriuretic peptide or the pulmonary surfactant protein as specified above with a sample comprising the natriuretic peptide or the a pulmonary surfactant protein and (b) measuring the amount of the natriuretic peptide or the pulmonary surfactant protein which is bound to the support.

The ligand is preferably selected from the group consisting of nucleic acids, peptides, polypeptides, antibodies and aptamers, and is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan J P, Sklar L A. (2002). Suspension array technology: evolution of the flat-array paradigm. Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744,305).

The term "amount" as used herein encompasses the absolute amount of the natriuretic peptides or the pulmonary surfactant protein, the relative amount or concentration of the natriuretic peptides or the pulmonary surfactant protein as well as any value or parameter which correlates thereto. Such values or parameters comprise intensity signal values from all specific physical or chemical properties obtained from the natriuretic peptides or the pulmonary surfactant protein by direct measurements, e.g., intensity values in mass spectra or NMR spectra. Moreover all values or parameters which are obtained by indirect measurements specified elsewhere in this description are also encompassed, e.g., expression levels determined from biological read out systems in response to the natriuretic peptide or the pulmonary surfactant protein or intensity signals obtained from specifically bound ligands. It is to be understood that values correlating to the aforementioned amounts or parameters can also be obtained by all standard mathematical operations.

Pulmonary surfactant proteins are proteins, which, under physiological conditions, are found pivotally in the pulmonary surfactant of a subject. These pulmonary surfactant proteins are surfactant protein A (SP-A), surfactant protein B (SP-B) and/or surfactant protein D (SP-D). In preferred embodiments, the term "pulmonary surfactant protein" as used herein refers to SP-B. The term, preferably, encompasses the human proteins as well as variants thereof, preferably, allelic variants or species specific homologs, paralogs or orthologs. The human surfactant proteins are well characterized in the prior art and disclosed, e.g., in Hawgood, 1989, Am J Physiol-Lung Cellular and Molecular Physiology, Vol 257, Issue 2:13-L22 (for all surfactant proteins), Takahashi 2006, Curr Pharm Des, 12(5):589-598 (for SP-A and SP-D), and Kurutz 2002, Biochemistry, 41(30):9627-9636, Guttentag 1998, Am J Physiol -Lung Cellular and Molecular Physiology, Vol 275, Issue 3:L559-L566 (for SP-B).

Also specifically envisaged are variants of pulmonary surfactant proteins which are on the amino acid level at least 60% identical, more preferably at least 70%, at least 80%, at least 90%, at least 95%, at least 98% or at least 99% identical, to the human pulmonary surfactant proteins. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of a human pulmonary surfactant protein as long as the said polypeptides have pulmonary surfactant protein properties. pulmonary surfactant protein properties as referred to herein are immunological and/or biological properties. Preferably, the pulmonary surfactant protein variants have immunological properties (i.e. epitope composition) comparable to those of the pulmonary surfactant proteins specifically referred to herein. Thus, the variants shall be recognizable by the aforementioned means or ligands used for determination of the pulmonary surfactant protein. Variants also include posttranslationally modified pulmonary surfactant proteins such as glycosylated proteins.

Moreover, it is to be understood that the term also encompasses any combination of the aforemtioned specific pulmonary surfactant proteins or variants thereof. For example, SP-B may be determined in combination with SP-D or SP-A or both.

As used herein, the term "natriuretic peptide" comprises Atrial Natriuretic Peptide (ANP)-type and Brain Natriuretic Peptide (BNP)-type peptides and variants thereof having the same predictive potential. Natriuretic peptides according to the present invention comprise ANP-type and BNP-type peptides and variants thereof(see e.g. Bonow, R. O. (1996). New insights into the cardiac natriuretic peptides. Circulation 93: 1946-1950).

Exemplary ANP-type peptides comprise pre-proANP, proANP, NT-proANP, and ANP.

Exemplary BNP-type peptides comprise pre-proBNP, proBNP, NT-proBNP, and BNP.

The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP, 28 amino acids in the case of ANP).

Preferred natriuretic peptides according to the present invention are NT-proANP, ANP, NT-proBNP, BNP, and variants thereof. ANP and BNP are the active hormones and have a shorter half-life than their respective inactive counterparts, NT-proANP and NT-proBNP. BNP is metabolised in the blood, whereas NT-proBNP circulates in the blood as an intact molecule and as such is eliminated renally. The in-vivo half-life of NTproBNP is 120 min longer than that of BNP, which is 20 min (Smith M W, Espiner E A, Yandle T G, Charles C J, Richards A M. Delayed metabolism of human brain natriuretic peptide reflects resistance to neutral endopeptidase. J Endocrinol. 2000; 167: 239-46.).

Preanalytics are more robust with NT-proBNP allowing easy transportation of the sample to a central laboratory (Mueller T, Gegenhuber A, Dieplinger B, Poelz W, Haltmayer M. Long-term stability of endogenous B-type natriuretic peptide (BNP) and amino terminal proBNP (NT-proBNP) in frozen plasma samples. Clin Chem Lab Med 2004; 42: 942-4.). Blood samples can be stored at room temperature for several days or may be mailed or shipped without recovery loss. In contrast, storage of BNP for 48 hours at room temperature or at 4° Celsius leads to a concentration loss of at least 20% (Mueller T, Gegenhuber A, et al., Clin Chem Lab Med 2004; 42: 942-4, supra; Wu A H, Packer M, Smith A, Bijou R, Fink D, Mair J, Wallentin L, Johnston N, Feldcamp C S, Haverstick D M, Ahnadi C E, Grant A, Despres N, Bluestein B, Ghani F. Analytical and clinical evaluation of the Bayer ADVIA Centaur automated B-type natriuretic peptide assay in patients with heart failure: a multisite study. Clin Chem 2004; 50: 867-73.). Therefore, depending on the time-course or properties of interest, either measurement of the active or the inactive forms of the natriuretic peptide can be advantageous.

The most preferred natriuretic peptides according to the present invention are NT-proBNP or variants thereof. As briefly discussed above, the human NT-proBNP as referred to in accordance with the present invention is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913, Bonow 1996, New Insights into the cardiac natriuretic peptides. Circulation 93: 1946-1950. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein.

The NT-proBNP referred to in accordance with the present invention further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are immunological and/or biological properties. Preferably, the NT-proBNP variants have immunological properties (i.e. epitope composition) comparable to those of NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999. Development of a novel, N-Terminal-proBNP (NT-proBNP) assay with a low detection limit. Scand J Clin Invest 59:177-181), Yeo et al. (Yeo 2003. Multicenter evaluation of the Roche NT-proBNP assay and comparison to the Biosite Triage assay. Clinica Chimica Acta 338:107-115), and in Example 1, below. Variants also include posttranslationally modified natriuretic peptides such as glycosylated peptides.

A variant in accordance with the present invention is also a peptide or polypeptide which has been modified after collection of the sample, for example by covalent or non-covalent attachment of a label, particularly a radioactive or fluorescent label, to the peptide.

Moreover, it is to be understood that the term also relates to any combination of the aforementioned specific natriuretic peptides.

The term "sample" refers to a sample of a body fluid, to a sample of separated cells or to a sample from a tissue or an organ. Samples of body fluids can be obtained by well known techniques and include, for example, samples of blood, plasma, serum or urine. Tissue or organ samples may be obtained from any tissue or organ by, e.g., biopsy. Separated cells may be obtained from the body fluids or the tissues or organs by separating techniques such as centrifugation or cell sorting.

Comparing as used herein encompasses comparing the amount of the natriuretic peptide or the pulmonary surfactant protein comprised by the sample to be analyzed with an amount of a suitable reference source specified below in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e. automatically providing a differential diagnosis for the diseases referred to herein in a suitable output format.

The term "reference amount" as used herein refers to an amount which allows assessing whether a subject suffers from any one of the aforementioned diseases or disorders by a comparison as referred to above. Accordingly, the reference may either be derived from a subject suffering from (i) a pulmonary disease, (ii) a cardiovascular complication, (iii) a cardiovascular complication accompanied by a pulmonary disease or (iv) chronic dyspnea without cardiovascular or pulmonary causes, i.e. from a healthy subject with respect to cardiovascular complications and pulmonary diseases. It is to be understood that if a reference from a subject is used which suffers from a disease or combination of diseases, an amount of a peptide or protein in a sample of a test subject being essentially identical to said reference amount shall be indicative for the respective disease or combination of diseases. If a reference from a healthy subject is used, an amount of a peptide or protein in a sample of a test subject which significantly differs from the reference (i.e. from the normal values of the surfactant proteins and natriuretic peptides referred to herein) shall indicate a disease. The reference amount applicable for an individual subject may vary depending on various physiological parameters such as age, gender, or subpopulation. Thus, a suitable reference amount may be determined by the method of the present invention from a reference sample to be analyzed together, i.e. simultaneously or subsequently, with the test sample. It has been found that an amount of a natriuretic peptide larger than the normal range (80 to 150 pg/ml and, preferably, 125 pg/ml) and an amount larger than the normal range of the blood pulmonary surfactant protein amount (12,000 to 20,000 ng/ml and, preferably, 20,000 ng/ml) is indicative of a cardiovascular complication accompanied by a pulmonary disease rather than of a pulmonary disease or a cardiovascular complication showing pulmonary symptoms as the cause of the dyspnea. It is to be understood that the aforementioned amounts may vary due to statistics and errors of measurement. A determination of elevated amounts for the pulmonary surfactant protein, but no elevated amounts of the natriuretic peptides, indicates that the subject suffers from a pulmonary disease. A determination that the amounts of the natriuretic peptide and the surfactant protein are both elevated with respect to the normal ranges indicates that the subject suffers from a cardiovascular complication accompanied by a pulmonary disease. A determination that the amount of the natriuretic peptide is elevated solely indicates that the subject suffers from a cardiovascular complication. Finally, a determination that none of the determined amounts is elevated with respect to the reference indicates that the subject exhibits chronic dyspnea due to non-cardiovascular, non-pulmonary causes specified elsewhere in this description.

Advantageously and unexpectedly, it has been found that the amount of pulmonary surfactant protein in combination with the amount of NT-pro BNP present in a sample of a subject showing pulmonary symptoms, in particular, shortness of breath, allow for a differential diagnosis with respect to the cause of the symptoms. The present invention beneficially enables subjects, in particular, emergency patients, to be more readily and reliably diagnosed and subsequently treated according to the result of the differential diagnosis.

The explanations and definitions of the terms made above and herein below apply accordingly for all embodiments characterized in this specification and the claims.

The following embodiments are particularly preferred embodiments of the method of the present invention.

According to a preferred embodiment of the method of the present invention, the pulmonary disease of the cardiovascular complication accompanied by a pulmonary disease (see (iii), above) is caused by the cardiovascular complication.

In a preferred embodiment of the method of the present invention, the cardiovascular complication of (iii) is caused by the pulmonary disease.

In another preferred embodiment of the method of the present invention, the pulmonary disease of (iii) is independent on the cardiovascular complication.

In a furthermore preferred embodiment of the method of the present invention, a reference amount less than 125 pg/ml for the natriuretic peptide and a reference amount larger than 20,000 ng/ml for a pulmonary surfactant protein are indicative of (i) a pulmonary disease.

In a furthermore preferred embodiment of the method of the present invention, a reference amount larger than 125 pg/ml for the natriuretic peptide and a reference amount less than 20,000 ng/ml for a pulmonary surfactant protein are indicative of (ii) a cardiovascular complication.

In a further preferred embodiment of the method of the present invention, a reference amount of larger than 125 pg/ml for the natriuretic peptide and a reference amount lager than 20,000 ng/ml for a pulmonary surfactant protein are indicative of (iii) a pulmonary disease accompanied by a cardiovascular complication.

In another preferred embodiment of the method of the present invention, a reference amount less than 125 pg/ml for the natriuretic peptide and a reference amount less than 20,000 ng/ml for a pulmonary surfactant protein are indicative of (iv) chronic dyspnea without cardiovascular or pulmonary causes.

Also, in a preferred embodiment of the method of the present invention, said sample is blood, plasma, serum or urine.

In another preferred embodiment of the method of the present invention, said natriuretic peptide is NT-proBNP.

Moreover, in a preferred embodiment of the method of the present invention, said subject is a human.

The present invention further relates to a device for differentiating cause of chronic dyspnea between (i) a pulmonary disease, (ii) a cardiovascular complication showing pulmonary symptoms, (iii) a cardiovascular complication accompanied by a pulmonary disease and (iv) dyspnea without cardiovascular or pulmonary causes in a subject exhibiting chronic dyspnea. The device comprises: means for determining concentration of a pulmonary surfactant protein in a sample of a subject; means for determining an amount of a natriuretic peptide or a variant thereof in a sample of a subject; and means for comparing the concentration and amount determined with a suitable reference, whereby cause of chronic dyspnea is differentiated between (i) a pulmonary disease, (ii) a cardiovascular complication, (iii) a cardiovascular complication accompanied by a pulmonary disease or (iv) chronic dyspnea without cardiovascular or pulmonary causes.

The term "device" as used herein relates to a system of means comprising at least the aforementioned means operatively linked to each other as to allow the prediction. Preferred means for determining the amount of the natriuretic peptides or the pulmonary surfactant protein and means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to diagnose or distinguish between the diseases referred to herein. Preferably, the means are comprised by a single device in such a case. Said device may accordingly include an analyzing unit for the measurement of the amount of the peptides in a sample and a computer unit for processing the resulting data for the differential diagnosis.

Alternatively, where means such as test stripes are used for determining the amount of the peptides, the means for diagnosing may comprise control stripes or tables allocating the determined amount to an amount known to be accompanied with (i) a pulmonary disease, (ii) a cardiovascular complication, (iii) a cardiovascular complication accompanied by a pulmonary disease or (iv) chronic dyspnea without cardiovascular or pulmonary causes or a healthy control subject. The test stripes are, preferably, coupled to a ligand which specifically binds to the natriuretic peptide or pulmonary surfactant protein. The strip or device, preferably, comprises means for detection of the binding of said peptides to the said ligand. Preferred means for detection are disclosed in connection with embodiments relating to the method of the invention above. In such a case, the means are operatively linked in that the user of the system brings together the result of the determination of the amount and the diagnostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test stripes or electronic devices which merely require loading with a sample. The results may be given as output of diagnostic raw data which need interpretation by the clinician. Preferably, the output of the device are, however, processed diagnostic raw data the interpretation of which does not require a specialized clinician. Further preferred devices comprise the analyzing units/devices (e.g., biosensors, arrays, solid supports coupled to ligands specifically recognizing the natriuretic peptide, Plasmon surface resonance devices, NMR spectrometers, mass-spectrometers etc.) or evaluation units/devices referred to above in accordance with the method of the invention.

Finally, the present invention relates to a kit for carrying out the methods of the present invention, wherein said kit comprises means for determining concentration of a pulmonary surfactant protein in a sample of a subject; means for determining an amount of a natriuretic peptide or a variant thereof in a sample of a subject; and means for comparing the concentration and amount determined with a suitable reference, whereby (i) a pulmonary disease, (ii) a cardiovascular complication, (iii) a cardiovascular complication accompanied by a pulmonary disease or (iv) chronic dyspnea without cardiovascular or pulmonary causes as a cause of chronic dyspnea can be differentiated.

The term "kit" as used herein refers to a collection of the aforementioned means, preferably, provided in separately or within a single container. The container, also preferably, comprises instructions for carrying out the method of the present invention.

All references cited in this specification are herewith incorporated by reference with respect to their entire disclosure content and the disclosure content specifically mentioned in this specification.

The following Example is intended to illustrate certain embodiments of the present invention and should not be construed to limit the scope of the invention as defined by the claims.

EXAMPLE

Study on patients with chronic dyspnea.

A cohort of 214 patients suffering from chronic dyspnea is clinically investigated for the presence of heart failure, pulmonary disease or a combination of both diseases. The allocation of the patients into the three disease groups is confirmed by clinical examination, ECG and echocardiography. Blood samples of the patients are analyzed by the prototype SP-B ELISA (Flinders assay protocol for the SP-B amounts and by the Elecsys NT-proBNP™ assay (Roche Diagnostics) for NT-proBNP concentrations.

Results of determination of the NT-proBNP concentration is shown in FIG. 1. Patients suffering from a combination of both diseases (heart failure and pulmonary disease) show elevated NT-proBNP levels, patients suffering from heart failure also show strongly elevated NT-proBNP levels. However, patients suffering from pulmonary disease only show normal NT-proBNP levels.

Figure 2:
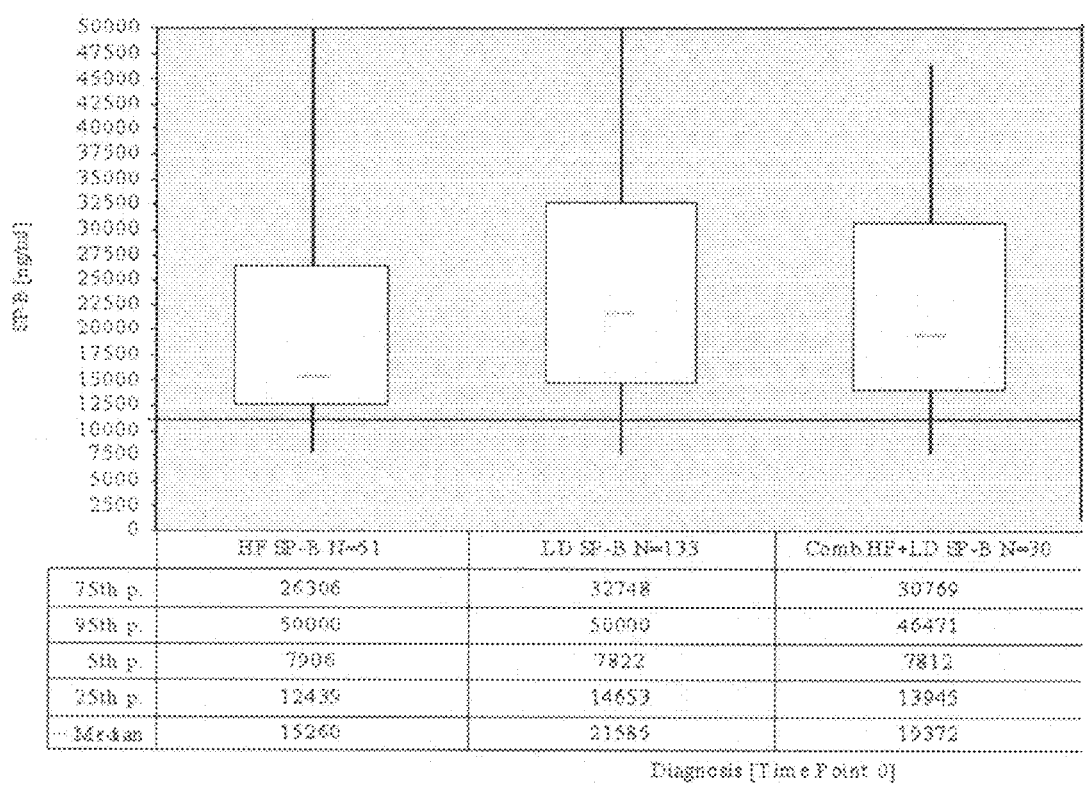
FIG. 2: The figure shows box plots for the SP-B concentration measured for a patient cohort having either heart failure (HF), a pulmonary disease (LD) or both (Comb. HF+LD). N represents the number of patients. Moreover, indicated are the median and the 75th, 95th, 5th and 25th percentiles.

FIG. 2 shows the outcome of the determination of the SP-B amount in the different patient groups. Patients with heart failure exhibit lower SP-B levels (normal SP-B levels) as compared to patients with pulmonary disorders (pulmonary disease) or patients suffering from pulmonary disorders and heart failure.

The invention claimed is:

1. A method for differentiating cause in a subject suffering from chronic shortness of breath (dyspnea) between (i) a pulmonary disease, (ii) a cardiovascular complication, (iii) a cardiovascular complication accompanied by a pulmonary disease, and (iv) dyspnea without cardiovascular or pulmonary causes, the method comprising the steps of:
    determining an amount of a pulmonary surfactant protein B (SP-B) in a sample from a subject;
    determining an amount of N-terminal pro brain natriuretic peptide (NT-proBNP) in a sample from said subject; and
    differentiating between (i) a pulmonary disease, (ii) a cardiovascular complication, (iii) a cardiovascular complication accompanied by a pulmonary disease and (iv) chronic dyspnea without cardiovascular or pulmonary causes by comparing the amount of SP-B determined to a reference amount of SP-B and the amount of NT-proBNP determined to a reference amount of NT-proBNP.

2. A method of differentially diagnosing a patient exhibiting dyspnea, the method comprising: application of the method according to claim 1, wherein the subject is a patient and determination only of an elevated amount of the SP-B indicates a diagnosis of a pulmonary disease, whereas determination of an elevated amount of both NT-proBNP and the SP-B indicates a diagnosis of a cardiovascular complication accompanied by a pulmonary disease, whereas determination only of an elevated amount of NT-proBNP indicates diagnosis of a cardiovascular complication, and whereas a determination of neither an elevated amount of NT-proBNP nor SP-B indicates diagnosis of chronic dyspnea due to non-cardiovascular, non-pulmonary causes, wherein an amount is elevated if it is greater by comparison with a reference amount.

3. The method according to claim 1, wherein a reference amount of less than 125 pg/ml for NT-proBNP and a reference amount of greater than 20,000 ng/ml for SP-B are indicative of (i) a pulmonary disease.

4. The method according to claim 1, wherein a reference amount of greater than 125 pg/ml for NT-proBNP and a reference amount of less than 20,000 ng/ml for SP-B are indicative of (ii) a cardiovascular complication.

5. The method according to claim 1, wherein a reference of amount of greater than 125 pg/ml for NT-proBNP and a reference amount of greater than 20,000 ng/ml for SP-B are indicative of (iii) a pulmonary disease accompanied by a cardiovascular complication.

6. The method according to claim 1, wherein a reference amount of less than 125 pg/ml for NT-proBNP and a reference amount of less than 20,000 ng/ml for SP-B are indicative of (iv) dyspnea without cardiovascular or pulmonary causes.

7. The method according to claim 1, wherein the sample comprises blood, plasma, serum or urine.

8. The method according to claim 1, wherein the subject is a human.

9. The method according to claim 1, wherein the pulmonary disease in (iii) is caused by the cardiovascular complication in (iii).

10. The method according to claim 1, wherein the cardiovascular complication in (iii) is caused by the pulmonary disease in (iii).

11. The method according to claim 1, wherein the pulmonary disease in (iii) is independent of the cardiovascular complication in (iii).

* * * * *